(12) United States Patent
Krishna et al.

(10) Patent No.: US 7,905,906 B2
(45) Date of Patent: Mar. 15, 2011

(54) SYSTEM AND METHOD FOR LUMBAR ARTHROPLASTY

(75) Inventors: Manoj Krishna, Yarm (GB); Tai Friesem, Barwick (GB)

(73) Assignee: Disc Motion Technologies, Inc., Boca Raton, FL (US)

( * ) Notice: Subject to any disclaimer, the term of this patent is extended or adjusted under 35 U.S.C. 154(b) by 651 days.

(21) Appl. No.: 11/594,716

(22) Filed: Nov. 8, 2006

(65) Prior Publication Data

US 2007/0288094 A1 Dec. 13, 2007

Related U.S. Application Data

(60) Provisional application No. 60/812,032, filed on Jun. 8, 2006.

(51) Int. Cl.
*A61B 17/70* (2006.01)

(52) U.S. Cl. ...................... 606/257; 623/17.15

(58) Field of Classification Search .................... 606/61, 606/246–249, 279, 250–253, 257, 258, 261; 623/17.11–17.16
See application file for complete search history.

(56) References Cited

U.S. PATENT DOCUMENTS

| | | | |
|---|---|---|---|
| 5,258,031 A | 11/1993 | Salib et al. | |
| 5,314,477 A | 5/1994 | Marnay | |
| 5,375,823 A | 12/1994 | Navas | |
| 5,401,269 A | 3/1995 | Buttner-Janz et al. | |
| 5,423,816 A | 6/1995 | Lin | |
| 5,425,773 A | 6/1995 | Boyd et al. | |
| 5,480,401 A | 1/1996 | Navas | |
| 5,507,816 A | 4/1996 | Bullivant | |
| 5,556,431 A | 9/1996 | Buttner-Janz | |
| 5,562,736 A | 10/1996 | Ray et al. | |
| 5,562,737 A | 10/1996 | Graf | |
| 5,562,738 A | 10/1996 | Boyd et al. | |
| 5,672,175 A | 9/1997 | Martin | |
| 5,676,701 A | 10/1997 | Yuan et al. | |
| 5,733,284 A | 3/1998 | Martin | |
| 5,899,941 A | 5/1999 | Nishijima et al. | |
| 6,019,792 A | 2/2000 | Cauthen | |
| 6,039,763 A | 3/2000 | Shelokov | |
| 6,063,121 A | 5/2000 | Xavier et al. | |
| 6,113,637 A | 9/2000 | Gill et al. | |
| 6,228,118 B1 | 5/2001 | Gordon | |
| 6,241,730 B1 | 6/2001 | Alby | |
| 6,283,968 B1 | 9/2001 | Mehdizadeh | |
| 6,368,350 B1 | 4/2002 | Erickson et al. | |
| 6,402,750 B1 | 6/2002 | Atkinson et al. | |
| 6,436,098 B1 | 8/2002 | Michelson | |

(Continued)

FOREIGN PATENT DOCUMENTS

EP 1647243 A2 4/2006

(Continued)

*Primary Examiner* — Eduardo C Robert
*Assistant Examiner* — Christina Negrelli
(74) *Attorney, Agent, or Firm* — Christopher & Weisberg, P.A.

(57) ABSTRACT

A system and method for lumbar arthroplasty in a spinal segment is provided having first and second vertebral bodies, where a intervertebral disc prosthesis may be positioned between the first and second vertebral bodies such that a center of rotation of movement of the vertebral bodies about the prosthesis is located substantially proximate to the upper endplate of the second vertebral body and substantially proximate to the posterior one-third portion of the second vertebral body. In addition, a stabilization element may be affixed to the first and second vertebral bodies such that a range of motion of the stabilization device defines a center of rotation substantially proximate to that of the intervertebral disc prosthesis.

15 Claims, 7 Drawing Sheets

U.S. PATENT DOCUMENTS

| | | |
|---|---|---|
| 6,440,168 B1 | 8/2002 | Cauthen |
| 6,471,724 B2 * | 10/2002 | Zdeblick et al. ............ 623/17.16 |
| 6,520,996 B1 | 2/2003 | Manasas et al. |
| 6,527,804 B1 | 3/2003 | Gauchet et al. |
| 6,540,785 B1 | 4/2003 | Gill et al. |
| 6,579,320 B1 | 6/2003 | Gauchet et al. |
| 6,626,905 B1 | 9/2003 | Schmiel et al. |
| 6,669,729 B2 | 12/2003 | Chin |
| 6,679,915 B1 | 1/2004 | Cauthen |
| 6,682,562 B2 | 1/2004 | Viart et al. |
| 6,706,068 B2 | 3/2004 | Ferree |
| 6,726,720 B2 | 4/2004 | Ross et al. |
| 6,733,532 B1 | 5/2004 | Gauchet et al. |
| 6,770,095 B2 | 8/2004 | Grinberg et al. |
| 6,802,867 B2 | 10/2004 | Manasas et al. |
| 6,830,570 B1 | 12/2004 | Frey et al. |
| 6,835,205 B2 | 12/2004 | Atkinson et al. |
| 6,852,128 B2 | 2/2005 | Lange |
| 6,878,167 B2 | 4/2005 | Ferree |
| 6,936,070 B1 | 8/2005 | Muhanna |
| 6,936,071 B1 | 8/2005 | Marnay et al. |
| 6,945,974 B2 | 9/2005 | Dalton |
| 6,972,037 B2 | 12/2005 | Zubok et al. |
| 6,974,478 B2 | 12/2005 | Reiley et al. |
| 6,986,771 B2 | 1/2006 | Paul et al. |
| 6,986,789 B2 | 1/2006 | Schultz et al. |
| 6,989,011 B2 | 1/2006 | Paul et al. |
| 6,994,727 B2 | 2/2006 | Khandkar et al. |
| 7,001,432 B2 | 2/2006 | Keller et al. |
| 7,014,633 B2 | 3/2006 | Cragg |
| 7,025,787 B2 | 4/2006 | Bryan et al. |
| 7,029,475 B2 | 4/2006 | Panjabi |
| 7,033,392 B2 | 4/2006 | Schmiel et al. |
| 7,037,340 B2 | 5/2006 | Gau |
| 7,041,136 B2 | 5/2006 | Goble et al. |
| 7,048,764 B2 | 5/2006 | Ferree |
| 7,052,515 B2 | 5/2006 | Simonson |
| 7,074,237 B2 | 7/2006 | Goble et al. |
| 7,074,238 B2 | 7/2006 | Stinson et al. |
| 7,083,622 B2 | 8/2006 | Simonson |
| 7,083,649 B2 | 8/2006 | Zucherman et al. |
| 7,087,084 B2 | 8/2006 | Reiley |
| 7,090,698 B2 | 8/2006 | Goble et al. |
| 7,204,852 B2 | 4/2007 | Marnay et al. |
| 7,270,681 B2 | 9/2007 | Cauthen |
| 7,282,065 B2 | 10/2007 | Kirschman |
| 7,291,150 B2 | 11/2007 | Graf |
| 7,326,210 B2 | 2/2008 | Jahng et al. |
| 7,329,258 B2 | 2/2008 | Studer |
| 2004/0010316 A1 | 1/2004 | William et al. |
| 2004/0158254 A1 | 8/2004 | Eisermann |
| 2004/0176772 A1 | 9/2004 | Zubok et al. |
| 2004/0181285 A1 | 9/2004 | Simonson |
| 2004/0236329 A1 | 11/2004 | Panjabi |
| 2005/0043800 A1 | 2/2005 | Paul et al. |
| 2005/0049592 A1 | 3/2005 | Keith et al. |
| 2005/0049708 A1 | 3/2005 | Atkinson et al. |
| 2005/0154461 A1 | 7/2005 | Humphreys et al. |
| 2005/0154464 A1 | 7/2005 | Humphreys et al. |
| 2005/0154466 A1 | 7/2005 | Humphreys et al. |
| 2005/0154467 A1 | 7/2005 | Peterman et al. |
| 2005/0171543 A1 | 8/2005 | Timm et al. |
| 2005/0171610 A1 | 8/2005 | Humphreys et al. |
| 2005/0177156 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0222569 A1 | 10/2005 | Panjabi |
| 2005/0245930 A1 | 11/2005 | Timm et al. |
| 2005/0256578 A1 | 11/2005 | Blatt et al. |
| 2005/0277938 A1 | 12/2005 | Parsons |
| 2006/0069438 A1 | 3/2006 | Zucherman et al. |
| 2006/0069441 A1 | 3/2006 | Zucherman et al. |
| 2006/0079896 A1 * | 4/2006 | Kwak et al. ..................... 606/61 |
| 2006/0084994 A1 | 4/2006 | Atkinson et al. |
| 2006/0184171 A1 | 8/2006 | Biedermann et al. |
| 2006/0189984 A1 | 8/2006 | Fallin et al. |
| 2006/0247779 A1 * | 11/2006 | Gordon et al. ............. 623/17.15 |
| 2006/0265074 A1 | 11/2006 | Krishna et al. |
| 2007/0179616 A1 | 8/2007 | Braddock, Jr. et al. |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0270862 A1 | 11/2007 | Yu et al. |

FOREIGN PATENT DOCUMENTS

| | | |
|---|---|---|
| WO | 2005112835 A2 | 12/2005 |

* cited by examiner

SYSTEM AND METHOD FOR LUMBAR ARTHROPLASTY

CROSS-REFERENCE TO RELATED APPLICATION

This application is related to and claims priority to U.S. Provisional Patent Application Ser. No. 60/812,032 filed Jun. 08, 2006, entitled SYSTEM AND METHOD FOR LUMBAR ARTHROPLASTY, the entirety of which is incorporated herein by reference.

STATEMENT REGARDING FEDERALLY SPONSORED RESEARCH OR DEVELOPMENT n/a

FIELD OF THE INVENTION

The present invention relates to a system and method for lumbar arthroplasty, and more particularly, to a system having a posterior lumbar disc replacement and a posterior dynamic stabilization device having matched centers of rotation.

BACKGROUND OF THE INVENTION

Prior to the availability of lumbar arthroplasty, interbody fusion was the primary treatment modality for symptomatic lumbar disc disease. This procedure could typically remove the pain generator from the disc, but results could also include at least some loss in the ability to absorb shock, as well as a reduction in the range of motion of the disc. As such, additional stress could be experienced and lead to further premature degeneration of the adjacent levels of the spinal segment.

Lumbar arthroplasty through the anterior approach has become well established as an alternative treatment modality for symptomatic lumbar disc disease. This allows the removal of the lumbar disc and restoration of normal load transmission through the disc, in addition to allowing preservation of motion in the treated segment. The main aims of lumbar arthroplasty are the removal of the pain generator, the restoration of normal loading across the disc, the maintenance of motion of the segment and therefore, the reduction of strain on the adjacent levels.

Each motion segment of the spine moves around an instantaneous center of rotation. The instantaneous axis of rotation is defined as the axis perpendicular to the plane of motion passing through a point in the vertebral body that does not move. For each spinal motion segment, this point is essentially the point about which the motion segment rotates, and is also referred to as the center of rotation. If the spine is altered in any way, such as with disc and facet degeneration or spinal implantation, this center of rotation shifts. In a normal disc this center of rotation moves during flexion-extension to form an ellipse, and is located next to the upper endplate of the lower vertebra in the posterior third of the disc. With the onset of degeneration, this center of rotation may shift in an unpredictable manner. Thus, a goal of spinal arthroplasty includes restoration of the axis of rotation as closely as possible to that of a natural, healthy spinal segment.

Following a disc replacement, it would be beneficial for the center of rotation of the artificial disc to approximate that of the normal disc. Matching the center of rotation could result in the normal movement of the facet joints without undue strain and with efficient load transfer at the operated and adjacent levels. On the other hand, if the center of rotation of the disc prosthesis is not similar to that of a normal, healthy segment, the facet joints may experience additional strain during movement, which could result in increased pain, hypertrophy and/or fusion. The adjacent levels may also experience additional strain due to a non-synchronous movement of the operated motion segment, which could further contribute to accelerated degeneration at adjacent levels of the spinal segment.

A posterior dynamic stabilization system may be provided in a spinal segment to provide some degree of controlled multiplanar motion. The primary motions of a spinal segment include flexion and extension having a center of rotation near the anatomic normal, as well as rotation and side bending to a lesser degree.

Posterior dynamic fixation devices are commonly fixed to the pedicles at both ends and allow some unconstrained motion, which is primarily linear motion of flexion and extension. These devices are typically used as an alternative to spinal fusion in the treatment of spinal stenosis and other pathologies, as they may provide a stabilizer for certain abnormal motions. They may also be used to stabilize a motion segment adjacent to a spinal fusion. However, as discussed above, if a device has a center of rotation different than that of a normal, healthy disc, it could result in abnormal load transfers to the adjacent segment and subsequent non-physiological movement at the treated segment.

With the development of posterior lumbar disc arthroplasty methods, this center of rotation becomes even more crucial. This is due to the prevailing trend that most posterior lumbar arthroplasty procedures may require a significant resection of the facet joints for insertion, leading to a stronger need for a posterior dynamic stabilizer device. If the centers of rotation of the disc arthroplasty and the posterior dynamic device are dissimilar, the resulting range of motion of the spinal segment may be substantially reduced and/or eliminated.

Accordingly, it would be desirable to provide a posterior lumbar disc replacement and/or a posterior dynamic stabilization device or facet replacement system which could be positioned to provide movement about a center of rotation substantially similar to that of a healthy, intact intervertebral disc. It would further be desirable to provide a posterior dynamic stabilization system which can continuously adjust to a moving center of rotation of the disc replacement, or, if used on its own, with that of the lumbar disc of that level.

SUMMARY OF THE INVENTION

The present invention advantageously provides a method and system for lumbar arthroplasty including a vertebral disc prosthesis may be provided for insertion between first and second vertebral bodies to provide for the movement and articulation thereof. The vertebral disc prosthesis may include an articulating surface and/or mechanism, such as a hinge, ball-and-joint type structure, or simply a contoured surface, each of which would provide for the articulation of the first and second vertebral bodies upon implantation of the disc prosthesis therebetween. Moreover, the movement afforded to the first and second vertebral bodies due to the intervertebral disc prosthesis may define a center of rotation or movement.

The present invention may further include a stabilization element affixed to both the first and second vertebral bodies to provide added support and/or to control the range of motion of the spinal segment. The stabilization element may provide a range of motion in conjunction with the movement of the first and second vertebral bodies, wherein the range of motion of the stabilization element defines a center of rotation and/or movement. For example, the stabilization element may include a first portion for engaging the first vertebral body, as well as a second portion for engaging the second vertebral body, wherein the first and second portions are movably coupled to each other to provide an arcuate path of movement having the defined center of rotation.

In a method of lumbar arthroplasty in accordance with the present invention, the intervertebral prosthesis may be positioned between first and second vertebral bodies. Additionally, one or more stabilization elements may be affixed to the vertebral bodies as well, using pedicle screws or other similar affixation elements. As previously discussed, the stabilization element defines a center of rotation, which may be positioned to closely approximate that of the normal motion of the spinal segment prior to implantation. In addition, the vertebral disc prosthesis may also be positioned such that its center of rotation closely approximates that of a normal disc. As a result, the vertebral disc prosthesis may be positioned such that its center of rotation is substantially proximate to and/or is synchronous with the center of rotation of the stabilization element, which in turn, is aligned with and/or matches the center of rotation of the natural spinal segment.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
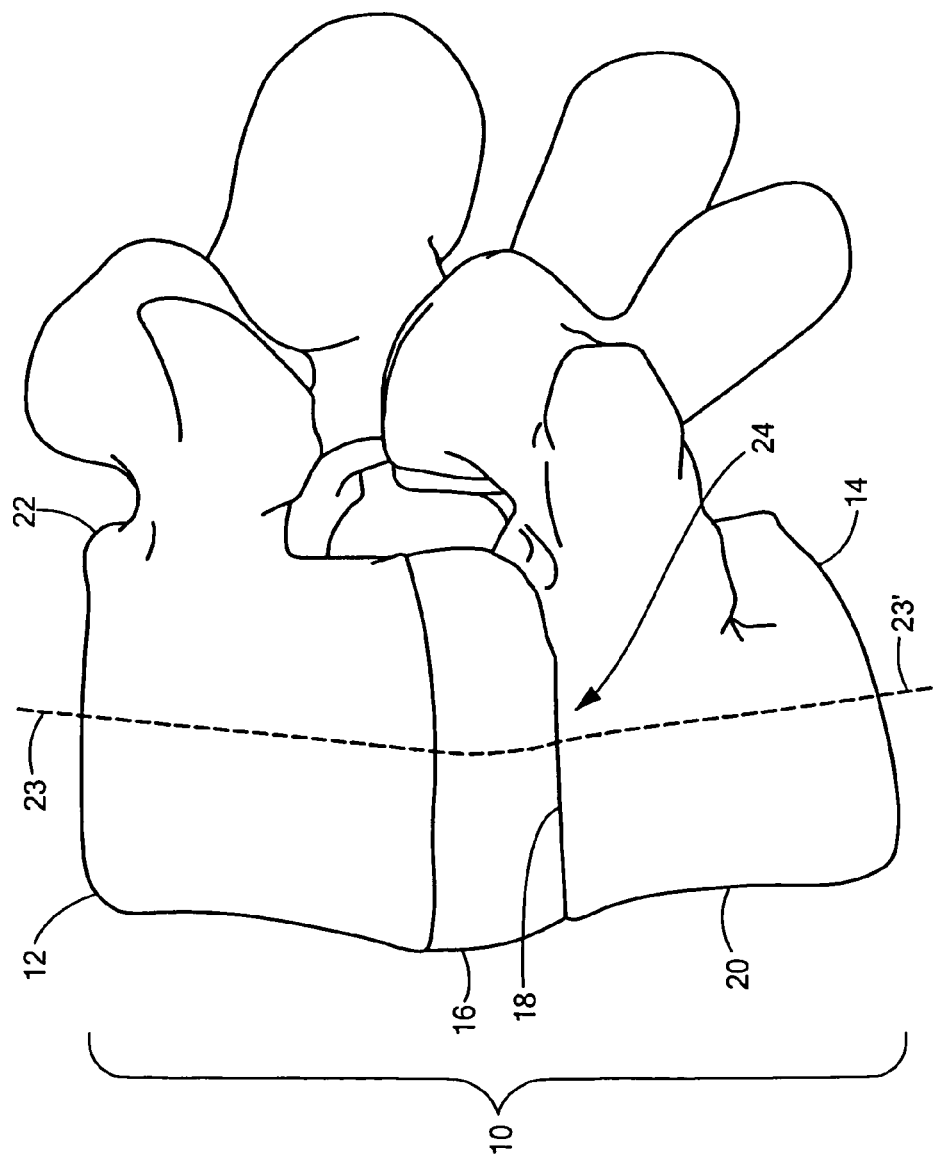
FIG. 1 is an illustration of a segment of a spinal column.

The present invention provides a system and method for spinal arthroplasty in a spinal segment. Primarily, the human spine consists of multiple spinal segments, with a spinal segment 10 having first and second vertebral bodies 12, 14 with an intervertebral disc 16 located therebetween, as shown in FIG. 1. Moreover, the spinal segment 10 typically includes a vertebral endplate 18, which is a thin layer of cartilage located between the vertebral body and the intervertebral disc 16. The vertebral bodies include both an anterior portion 20 and a posterior portion 22 corresponding to the "front" end and "back" end, respectively, of the spinal column as is known in the art. Each of the first and second vertebral bodies further define a midline 23, 23' equidistant from their respective anterior and posterior faces. As discussed above, each segment of the spine moves around an instantaneous point of rotation, where the point of rotation 24 is typically located next to the upper endplate 18 of the second vertebral body 14 towards substantially the posterior third of the second vertebral body 14. The exact position of a point of rotation 14 for a particular natural and healthy spinal segment of an individual may vary to some degree, and as such, variations may be identified through medical imaging techniques providing an illustration of the range of motion for a spinal segment of interest.

Figure 2:
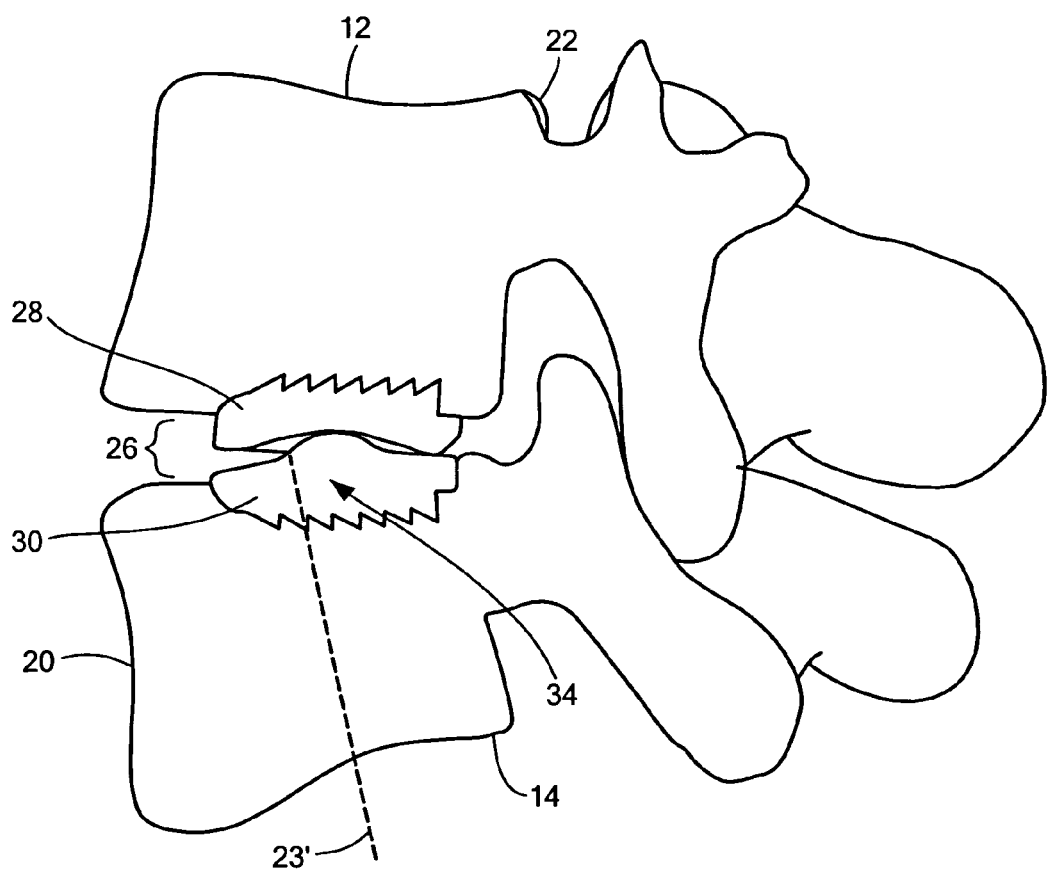
FIG. 2 depicts a first position of an embodiment of an intervertebral disc prosthesis of a system for lumbar arthroplasty in accordance with the present invention.
Figure 3:
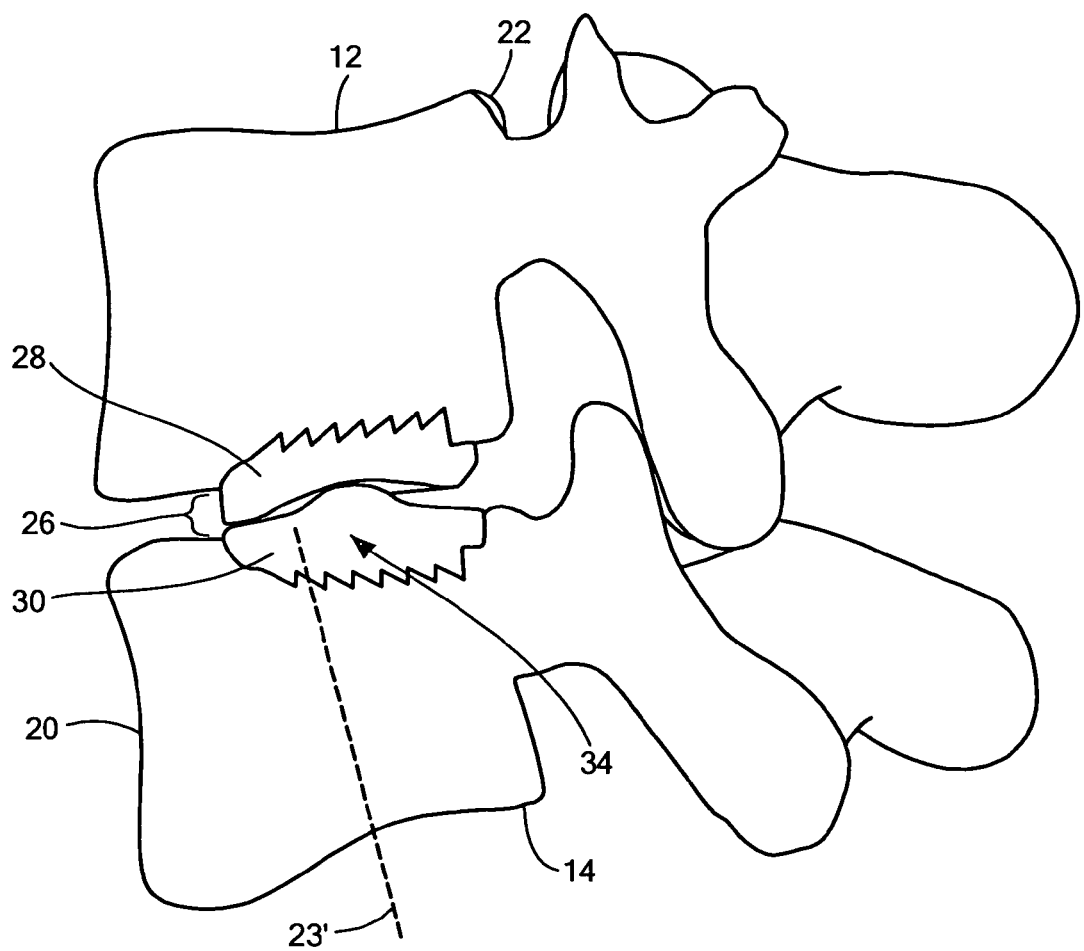
FIG. 3 shows a second position of an embodiment of an intervertebral disc prosthesis of a system for lumbar arthroplasty in accordance with the present invention.

Now referring to FIGS. 2-3, in a particular embodiment of the present invention, an intervertebral disc prosthesis 26 may be provided for insertion between the first and second vertebral bodies 12, 14 to provide for the movement and articulation thereof. In particular, the intervertebral disc prosthesis 26 may provide for the articulation of the first and second vertebral bodies across a range of motion similar to that which a natural intervertebral disc would provide. The intervertebral disc prosthesis 26 may include an articulating surface and/or mechanism, such as a hinge, ball-and-joint type structure, or simply a contoured surface, each of which would provide for the articulation of the first and second vertebral bodies upon implantation of the disc prosthesis therebetween. For example, the intervertebral disc prosthesis 26 may define a first portion 28 for engaging the first vertebral body 12, and a second portion 30 for engaging the second vertebral body 14. The first portion 28 may include a concave surface or depression, where the second portion 30 may include a rounded protrusion defining an articulating surface. Accordingly, the first and second portions of the prosthesis 26 may be movably coupled to each other such that the first and second portions are able to pivot, rotate, or otherwise move with respect to each other about the articulating surface as illustrated in the figures. Moreover, the movement between the first and second portions of the intervertebral disc prosthesis may define an axis of movement passing through a point of rotation 34 about which the two portions articulate during flexion and/or extension of the spinal segment. The location of the point of rotation 34 corresponds to the range of motion provided by the prosthesis 26, and may be affected by a particular dimension and/or geometric feature of the prosthesis 26, such as a radius of either of the concave depression and/or the rounded protrusion.

Of note, although an embodiment of a disc prosthesis has been provided where movement is achieved through the complementary movement of a concave depression and a rounded protrusion, it is recognized that there are a variety of ways in which movement may be provided between two vertebral bodies. For example, as mentioned above, a single disc component may be used which includes an arcuate protrusion in direct contact with a vertebral body to provide for the rotation and/or movement of the vertebral body directly thereon. In addition, various mechanisms and/or assemblies that allow a range of movement, such as hinges, single elements having shaped or contoured portions, compressible bodies, and the like, may be employed in accordance with the present invention. In addition, the particular dimensions and/or characteristics of an intervertebral prosthesis for a particular application may be modified, manipulated, and/or designed to provide a point of rotation at a desired location and/or distance from a reference point on the prosthesis or the spinal segment upon implantation.

Figure 4:
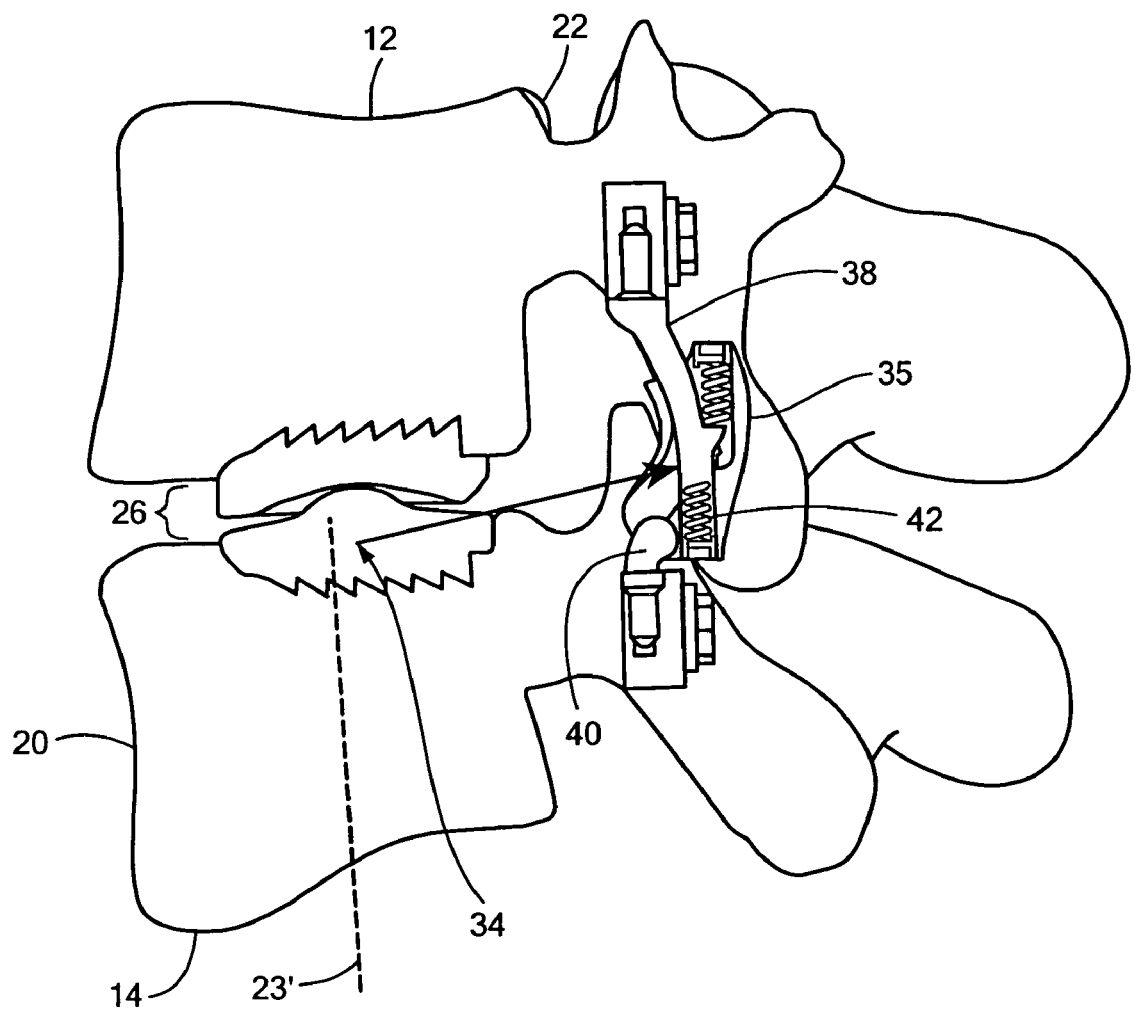
FIG. 4 illustrates a first position of an embodiment of a stabilization element of a system for lumbar arthroplasty in accordance with the present invention.
Figure 5:
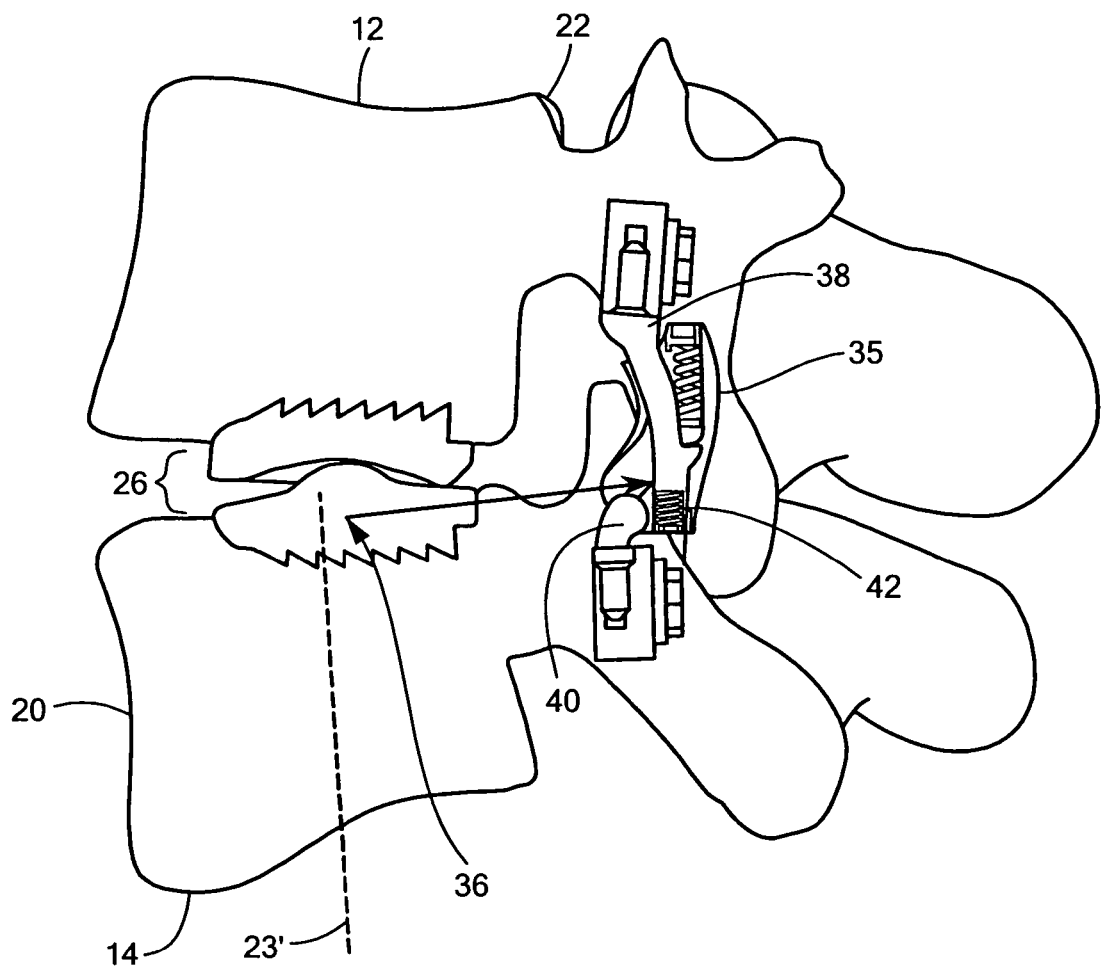
FIG. 5 depicts a second position of an embodiment of a stabilization element of a system for lumbar arthroplasty in accordance with the present invention.

Now referring to FIGS. 4-5, the present invention may further include a stabilization element 35 affixed to both the first and second vertebral bodies 12, 14 to provide added support and/or to control the range of motion of the spinal segment 10. Similar to that of the intervertebral disc prosthesis 26, the stabilization element 35 may provide a range of motion in conjunction with the movement of the first and second vertebral bodies, wherein the range of motion of the stabilization element 35 defines a point of rotation and/or movement 36. For example, the stabilization element 35 may include a first portion 38 for engaging the first vertebral body 12, as well as a second portion 40 for engaging the second vertebral body 14, wherein the first and second portions are movably coupled to each other. The first and second portions of the stabilization element 35 may be coupled through a sliding track that enables the first and second portion to provide an arcuate path of movement having the defined point of rotation 36.

As with the intervertebral disc prosthesis 26, the particular dimensions and/or characteristics of the stabilization element 35 may be modified and/or selected to provide a point of rotation at a desired location or distance from a reference point on the stabilization element 35 or the spinal segment 10. In addition, the stabilization element 35 may include a dampening element 42 such as a spring or other compressible body to alleviate and/or accommodate the forces experienced by the spinal segment at any particular time. The first and second portions of the stabilization element 35 may be affixed to the first and second vertebral bodies on the posterior portion 22 through the use of screws or other affixation elements as is known in the art. The distance that the stabilization element 35 may be offset from either of the first and second vertebral bodies due to the use of affixation elements may be taken into account when selecting the appropriate dimensions of the stabilization element 35 and/or upon positioning the stabilization element 35 to ensure the point of rotation 36 is at the desired location.

Figure 6:
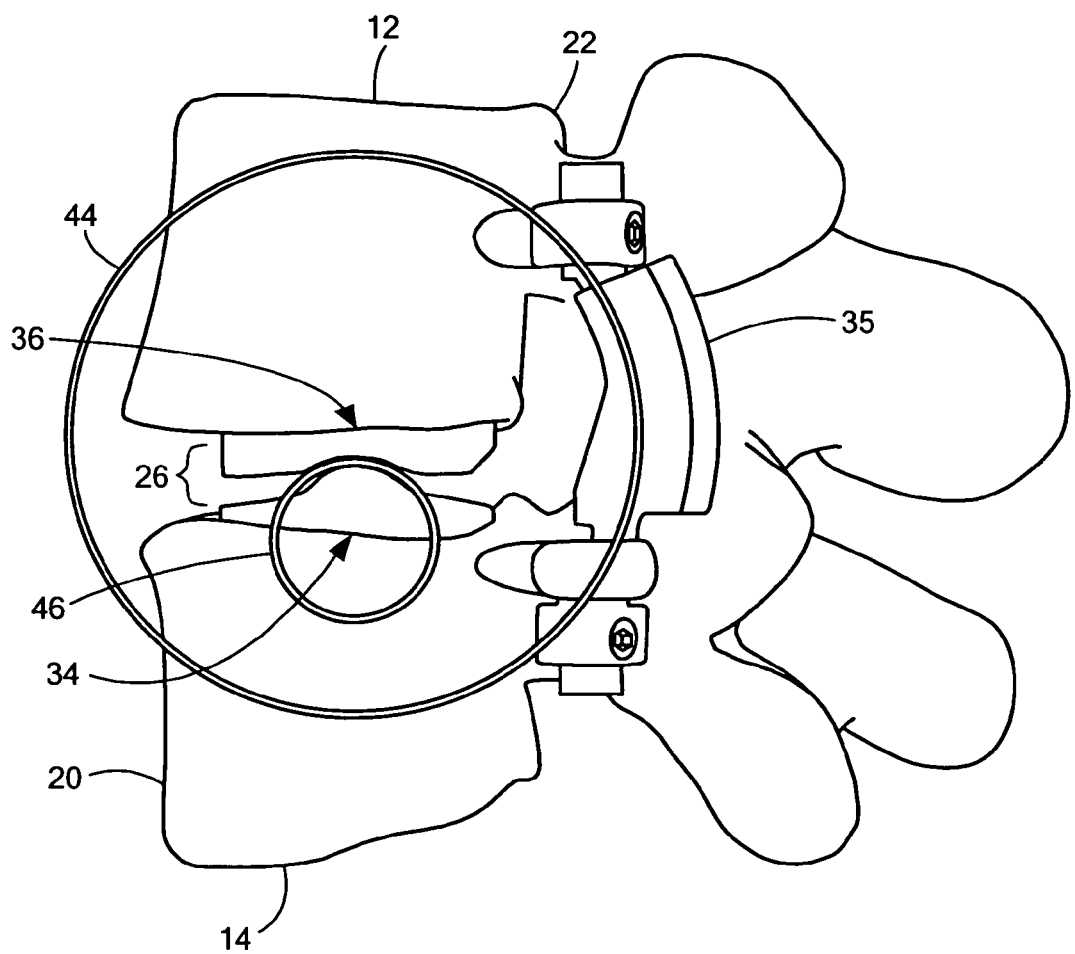
FIG. 6 shows a spinal segment having an embodiment of an intervertebral disc prosthesis and a stabilization element having misaligned centers of rotation.

Now referring to FIG. 6, a spinal motion segment is shown including the first and second vertebral bodies 12, 14 with the intervertebral disc prosthesis 26 placed therebetween. The stabilization element 35 is also shown affixed to the posterior side of the first and second vertebral bodies. As shown, the point of rotation 34 of the intervertebral disc prosthesis 26 is not located similarly to that of the point of rotation 36 of the stabilization element 35. As a result, this difference between the centers of rotation of the disc prosthesis 26 and the stabilization element 35 may prevent the motion segment 10 from moving comparably to the motion experienced by a natural, healthy segment. In addition, the mismatched centers of rotation may prevent the stabilization element 35 from moving in a desired range of motion, and instead causing increased stress at the affixation point where the stabilization element 35 is attached to the vertebral bodies. Moreover, as previously discussed, this misalignment may result in additional strain on movement, resulting in pain, hypertrophy or fusion, and may further contribute to augmented degeneration of the spinal segment 10.

Figure 7:
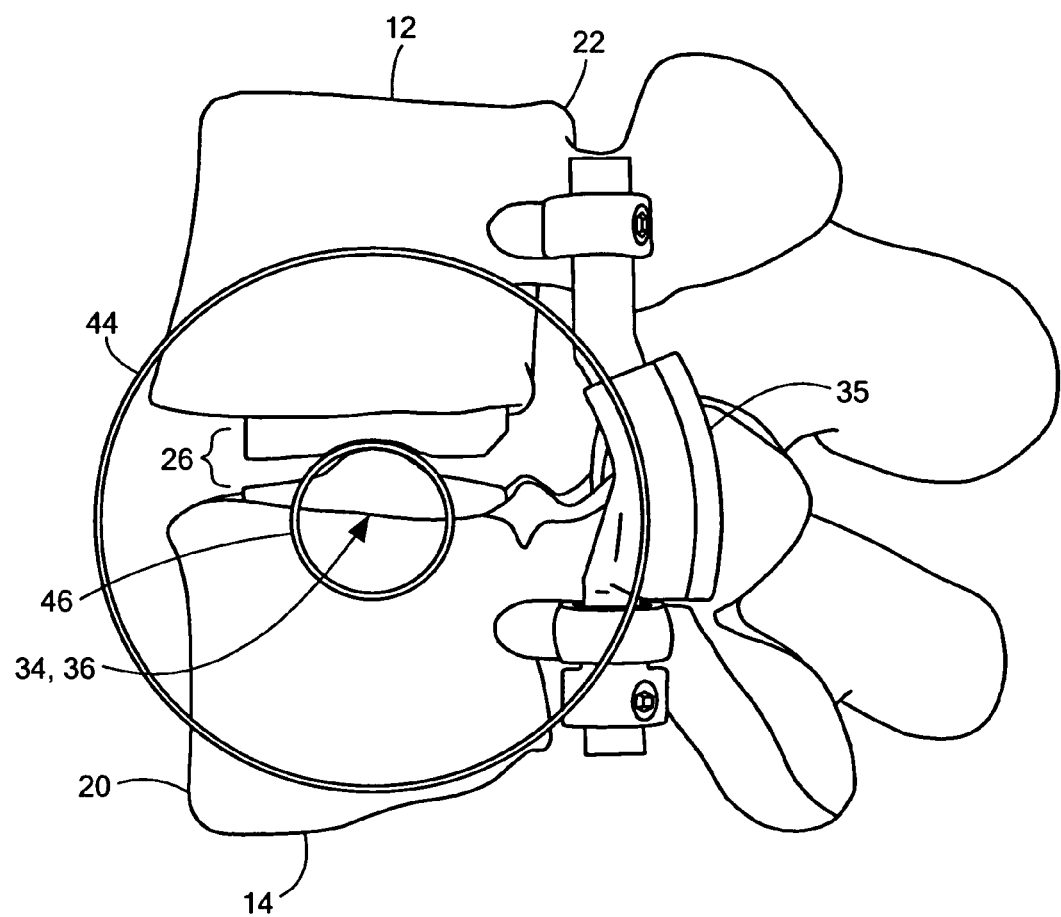
FIG. 7 illustrates an embodiment of a lumbar arthroplasty system having matched centers of rotation in accordance with the present invention.

Now referring to FIG. 7, in an exemplary use of the system for lumbar arthroplasty in accordance with the present invention, the intervertebral disc prosthesis 26 is inserted between the adjacent first and second vertebral bodies 12, 14. Of course, prior to positioning the intervertebral disc prosthesis, at least a portion of the natural intervertebral disc may have to be removed, and the endplate surfaces of the first and second vertebral bodies may require some preparation in order to properly receive the intervertebral disc prosthesis 26. Additionally, one or more stabilization elements 35 may be affixed to the vertebral bodies as well, using pedicle screws or other similar affixation elements. As previously discussed, the stabilization element 35 defines a point of rotation 36 and a motion range about a portion of a reference arc 44. The point of rotation 36 of the stabilization element 35 may be positioned to closely approximate that of the normal motion of the spinal segment 10 prior to implantation. The point of rotation may be located near the upper endplate of the second vertebral body 14 and offset from the midline 23' of the second vertebral body 14 towards the posterior face 22. Further, the point of rotation may be located from the posterior face 22 a distance approximately equal to one-third of the total distance between the anterior and posterior faces. Further, although the typical point of rotation has been suggested, there may be variations in the desired positioning of the point of rotation of an implanted device due the physiology or anatomical condition of the motion segment, which may be impacted by any degradation in the vertebral bodies.

The intervertebral disc prosthesis 26 also defines a point of rotation 34 and a motion range about a portion of a reference arc 46. The disc prosthesis 26 may also be positioned such that its point of rotation 34 closely approximates that of a normal disc as described above. As a result, the intervertebral disc prosthesis 26 may be positioned such that its point of rotation 34 is substantially proximate to and/or is synchronous with the point of rotation 36 of the stabilization element 35, which in turn, is aligned with and/or matches the point of rotation of the natural spinal segment. Of note, it is recognized that in some applications it may not be desirable to provide both the intervertebral disc prosthesis 26 and the stabilization element 35. Accordingly, it is contemplated that either the intervertebral disc prosthesis 26 or the stabilization element 35 may be implanted by itself, with the resulting point of rotation for either device being positioned in the desired location.

Once the intervertebral disc prosthesis 26 and/or the stabilization elements 35 are implanted, subsequent forces and movement experienced by the vertebral bodies will translate to the intervertebral disc implant 26 and the stabilization element 35, thus causing movement of the relative portions of those devices. For example, should the motion segment experience flexion, the first and second portions of the intervertebral disc prosthesis 26 (and thus the first and second vertebral bodies) will pivot and/or rotate about the point of rotation 34 of the intervertebral disc prosthesis 26. In addition, the first and second portions of the stabilization element 35 will also move about its point of rotation 36. Vice versa, should the two vertebral bodies experience an extension, the portions of the intervertebral disc prosthesis 26 and the stabilization element 35 will adjust accordingly. As the centers of rotation of the two components are aligned and/or matched, movement of the spinal segment having the implanted prostheses will approximate the natural physiological movement of the spinal segment prior to implantation of the devices.

In addition to providing an aligned and/or matched point of rotation between the intervertebral disc prosthesis 26 and the stabilization element 35 to provide proper physiological movement upon implantation, the stabilization element 35 may further provide the ability to continuously adjust to a moving center of rotation of the vertebral disc prosthesis, or that of a normal motion segment in the event a disc prosthesis is not implanted. The relative movement of the first and second portions of the stabilization element 35 may include several degrees of freedom, as well as a telescoping movement in order to readily accommodate the motion experienced by the spinal segment during the period of use of the stabilization element 35. For example, the stabilization element 35 may include a ball-and socket type joint on one of the first and second portions of the device to accommodate forces experienced while implanted and to adjust itself accordingly. This self-regulating feature may provide a safeguard against initial center-or-rotation mismatches introduced at the time of implantation, and may further regulate center-of-rotation deficits experienced during the course of use of the prostheses.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of performing spinal arthroplasty on a spinal segment having a superior vertebral body and an inferior vertebral body, wherein the inferior vertebral body defines an endplate, an anterior face, and a posterior face, comprising the step of:
    positioning an intervertebral prosthesis between the superior vertebral body and the inferior vertebral body such that the superior and inferior vertebral bodies are movable with respect to each other about a first point of rotation located a distance from the posterior face that is approximately one-third of the distance between the anterior face and the posterior face of the inferior vertebral body.

2. The method according to claim 1, wherein the first point of rotation is located substantially proximate to the endplate of the inferior vertebral body.

3. The method according to claim 1, wherein the intervertebral prosthesis defines a first portion for engaging the superior vertebral body, and a second portion for engaging the inferior vertebral body.

4. The method according to claim 3, wherein the first portion defines a concave depression, and the second portion defines a rounded protrusion.

5. A method of performing spinal arthroplasty on a spinal segment having a superior vertebral body and an inferior vertebral body, wherein the inferior vertebral body defines an endplate, an anterior face, a posterior face, and a midline therebetween, comprising the step of:
    coupling a stabilizing element to the superior and inferior vertebral bodies such that the superior and inferior vertebral bodies are movable with respect to each other about a first point of rotation located a distance from the posterior face that is approximately one-third of the distance between the anterior face and the posterior face of the second vertebral body.

6. The method according to claim 5, wherein the first point of rotation is located substantially proximate to the endplate of the inferior vertebral body.

7. A method of performing spinal arthroplasty on a spinal segment having a superior vertebral body and an inferior vertebral body, wherein the inferior vertebral body defines an endplate, an anterior face, a posterior face, and a midline therebetween, comprising the step of:
    coupling a stabilizing element defining a first portion movably coupled to a second portion to the superior and inferior vertebral bodies such that the superior and inferior vertebral bodies are movable with respect to each other about a first point of rotation offset from the midline of the inferior vertebral body between the midline and the posterior face.

8. The method according to claim 7, wherein the first and second portions of the stabilizing element are movable in an arcuate path.

9. A method of performing spinal arthroplasty on a spinal segment having a first vertebral body and a second vertebral body, wherein the second vertebral body defines an endplate, an anterior face, a posterior face, and a midline therebetween, comprising the step of:
    positioning an intervertebral prosthesis between the first vertebral body and the second vertebral body, such that the first and second vertebral bodies are movable with respect to each other about a first point of rotation located proximate to the endplate of the second vertebral body and offset from the midline of the second vertebral body;
    providing a stabilizing element having a range of motion defined about a second point of rotation; and
    coupling the stabilizing element to the first and second vertebral bodies such that the first point of rotation and the second point of rotation are at substantially the same location.

10. The method according to claim 9, wherein the first point of rotation is located between the midline and the posterior face of the second vertebral body.

11. The method according to claim 10, wherein the first point of rotation is located a distance from the posterior face that is approximately one-third of the distance between the anterior face and the posterior face.

12. The method according to claim 9, wherein the stabilizing element defines a first portion movably coupled to a second portion.

13. The method according to claim 12, wherein the first and second portions of the stabilizing element move in an arcuate path.

14. The method according to claim 9, wherein the intervertebral prosthesis defines a first portion for engaging the first vertebral body, and a second portion for engaging the second vertebral body.

15. The method according to claim 14, wherein the first portion defines a concave depression, and the second portion defines a rounded protrusion.

* * * * *